(12) United States Patent
Raybuck

(10) Patent No.: US 7,306,566 B2
(45) Date of Patent: Dec. 11, 2007

(54) NEEDLE FREE BLOOD COLLECTION DEVICE WITH MALE CONNECTOR VALVE

(75) Inventor: John Raybuck, Los Angeles, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 366 days.

(21) Appl. No.: 10/941,225

(22) Filed: Sep. 15, 2004
(Under 37 CFR 1.47)

(65) Prior Publication Data

US 2006/0058773 A1 Mar. 16, 2006

(51) Int. Cl.
*A61B 5/00* (2006.01)

(52) U.S. Cl. .................................... 600/576

(58) Field of Classification Search ............ 600/573, 600/576, 577, 579, 575; 604/256; 251/149.1–149.6
See application file for complete search history.

(56) References Cited

U.S. PATENT DOCUMENTS

| | | |
|---|---|---|
| 2,931,668 A | 4/1960 | Baley |
| 2,968,497 A | 1/1961 | Treleman |
| 3,127,892 A | 4/1964 | Bellamy, Jr. et al. |
| 3,304,047 A | 2/1967 | Martin |
| 3,334,860 A | 8/1967 | Bolton, Jr. |
| 3,986,508 A | 10/1976 | Barrington |
| 4,066,067 A | 1/1978 | Micheli |
| 4,080,965 A | 3/1978 | Phillips |
| 4,121,585 A | 10/1978 | Becker, Jr. |
| 4,133,441 A | 1/1979 | Mittleman et al. |
| 4,195,632 A | 4/1980 | Parker et al. |
| 4,233,982 A | 11/1980 | Bauer et al. |
| 4,245,635 A | 1/1981 | Kontos |
| 4,340,049 A | 7/1982 | Munsch |
| 4,379,458 A | 4/1983 | Bauer et al. |
| 4,387,879 A | 6/1983 | Tauschinski |
| 4,397,442 A | 8/1983 | Larkin |
| 4,457,749 A | 7/1984 | Bellotti et al. |
| 4,511,359 A | 4/1985 | Vaillancourt |
| 4,623,332 A | 11/1986 | Lindmayer et al. |
| 4,662,878 A | 5/1987 | Lindmayer |
| 4,723,603 A | 2/1988 | Plummer |
| 4,774,964 A | 10/1988 | Bonaldo |
| 4,774,965 A | 10/1988 | Rodriguez et al. |
| 4,781,702 A | 11/1988 | Herrli |
| 4,816,024 A | 3/1989 | Sitar et al. |
| 4,834,271 A | 5/1989 | Litwin |
| 4,862,913 A | 9/1989 | Wildfang |
| 4,883,483 A | 11/1989 | Lindmayer |
| 4,915,687 A | 4/1990 | Sivert |
| 4,917,669 A | 4/1990 | Bonaldo |
| 4,935,010 A | 6/1990 | Cox et al. |

(Continued)

*Primary Examiner*—Max Hindenburg
*Assistant Examiner*—Sharick Naqi
(74) *Attorney, Agent, or Firm*—McDermott Will & Emery

(57) ABSTRACT

A needle free vacuumized blood collection device includes a male connector having a valve element disposed within the internal bore of the male connector that opens or closes a flow passage into the blood collection vial. The valve element includes an activation arm extending outwardly through the male connector that contacts a female connector when the male and female connector are engaged. The activation arm shifts the valve element in the proximal direction to open a naturally open flow opening in the valve element to permit flow into the vial. A spring device biases the valve element to the non-flow configuration.

21 Claims, 7 Drawing Sheets

U.S. PATENT DOCUMENTS

| | | |
|---|---|---|
| 4,950,260 A | 8/1990 | Bonaldo |
| 5,006,114 A | 4/1991 | Rogers et al. |
| 5,065,783 A | 11/1991 | Ogle, II |
| 5,070,885 A | 12/1991 | Bonaldo |
| 5,098,385 A | 3/1992 | Walsh |
| 5,108,376 A | 4/1992 | Bonaldo |
| 5,122,123 A | 6/1992 | Vaillancourt |
| 5,139,483 A | 8/1992 | Ryan |
| 5,147,333 A | 9/1992 | Raines |
| 5,154,703 A | 10/1992 | Bonaldo |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,211,634 A | 5/1993 | Vaillancourt |
| 5,215,537 A | 6/1993 | Lynn et al. |
| 5,215,538 A | 6/1993 | Larkin |
| 5,242,393 A | 9/1993 | Brimnall |
| 5,251,873 A | 10/1993 | Atkinson et al. |
| 5,269,771 A | 12/1993 | Thomas et al. |
| 5,273,533 A | 12/1993 | Bonaldo |
| 5,279,571 A | 1/1994 | Larkin |
| 5,281,206 A | 1/1994 | Lopez |
| 5,284,475 A | 2/1994 | Mackal |
| 5,295,657 A | 3/1994 | Atkinson |
| 5,306,243 A | 4/1994 | Bonaldo |
| 5,330,450 A | 7/1994 | Lopez |
| 5,334,159 A | 8/1994 | Turkel |
| 5,344,414 A | 9/1994 | Lopez et al. |
| 5,360,413 A | 11/1994 | Leason et al. |
| 5,370,636 A | 12/1994 | Von Witzleben |
| 5,380,306 A | 1/1995 | Brinon |
| 5,385,372 A | 1/1995 | Utterberg |
| 5,390,898 A | 2/1995 | Smedley et al. |
| 5,395,348 A | 3/1995 | Ryan |
| 5,397,314 A | 3/1995 | Farley et al. |
| 5,400,500 A | 3/1995 | Behnke et al. |
| 5,401,245 A | 3/1995 | Haining |
| 5,402,982 A | 4/1995 | Atkinson et al. |
| 5,405,323 A | 4/1995 | Rogers et al. |
| 5,405,331 A | 4/1995 | Behnke et al. |
| 5,405,333 A | 4/1995 | Richmond |
| 5,411,499 A | 5/1995 | Dudar et al. |
| 5,417,673 A | 5/1995 | Gordon |
| 5,423,791 A | 6/1995 | Bartlett |
| 5,425,465 A | 6/1995 | Healy |
| 5,433,330 A | 7/1995 | Yatsko et al. |
| 5,439,451 A | 8/1995 | Collinson et al. |
| 5,441,487 A | 8/1995 | Vedder |
| 5,456,668 A | 10/1995 | Ogle, II |
| 5,456,675 A | 10/1995 | Wolbring et al. |
| 5,464,399 A | 11/1995 | Boettger |
| 5,470,319 A | 11/1995 | Mayer |
| 5,470,327 A | 11/1995 | Helgren et al. |
| 5,474,536 A | 12/1995 | Bonaldo |
| 5,480,393 A | 1/1996 | Bommarito |
| 5,492,147 A | 2/1996 | Challender et al. |
| 5,501,426 A | 3/1996 | Atkinson et al. |
| 5,514,117 A | 5/1996 | Lynn |
| 5,518,026 A | 5/1996 | Benjey |
| 5,520,665 A | 5/1996 | Fleetwood |
| 5,533,708 A | 7/1996 | Atkinson et al. |
| 5,533,983 A | 7/1996 | Haining |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,552,118 A | 9/1996 | Mayer |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,584,819 A | 12/1996 | Kopfer |
| 5,597,536 A | 1/1997 | Mayer |
| 5,616,129 A | 4/1997 | Mayer |
| 5,616,130 A | 4/1997 | Mayer |
| RE35,539 E | 6/1997 | Bonaldo |
| 5,645,538 A | 7/1997 | Richmond |
| 5,674,206 A | 10/1997 | Allton et al. |
| 5,676,346 A | 10/1997 | Leinsing |
| 5,685,866 A | 11/1997 | Lopez |
| 5,738,144 A | 4/1998 | Rogers |
| RE35,841 E | 7/1998 | Frank et al. |
| 5,779,074 A * | 7/1998 | Burns ................. 215/247 |
| 5,782,816 A | 7/1998 | Werschmidt et al. |
| 5,806,831 A * | 9/1998 | Paradis ................. 251/149.1 |
| 5,820,601 A | 10/1998 | Mayer |
| 5,839,715 A | 11/1998 | Leinsing |
| 5,848,994 A | 12/1998 | Richmond |
| 6,029,946 A | 2/2000 | Doyle |
| 6,068,011 A | 5/2000 | Paradis |
| 6,079,432 A | 6/2000 | Paradis |
| 6,106,502 A | 8/2000 | Richmond |
| 6,113,068 A | 9/2000 | Ryan |
| 6,142,446 A | 11/2000 | Leinsing |
| 6,206,860 B1 | 3/2001 | Richmond |
| 6,290,206 B1 | 9/2001 | Doyle |
| 6,299,132 B1 | 10/2001 | Weinheimer et al. |
| 6,485,472 B1 | 11/2002 | Richmond |
| 6,541,802 B2 | 4/2003 | Doyle |
| 6,745,998 B2 | 6/2004 | Doyle |
| 7,140,592 B2 * | 11/2006 | Phillips ................. 251/149.6 |
| 2003/0032940 A1 | 2/2003 | Doyle |
| 2003/0060779 A1 | 3/2003 | Richmond |
| 2003/0136932 A1 * | 7/2003 | Doyle ................. 251/149.1 |
| 2003/0183795 A1 | 10/2003 | Doyle |
| 2004/0124389 A1 | 7/2004 | Phillips |

* cited by examiner

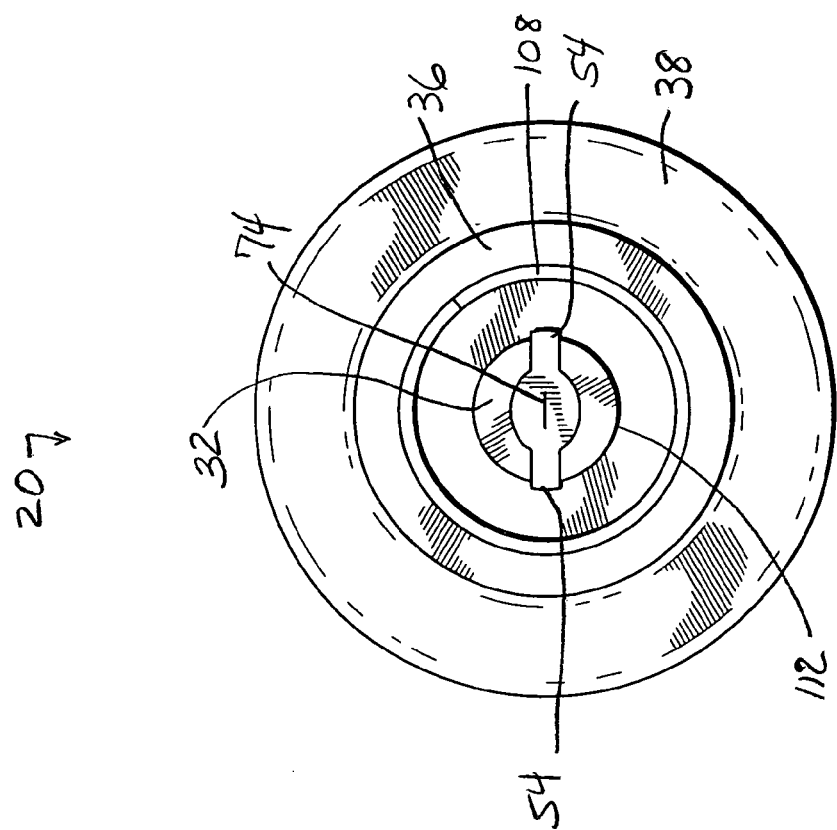
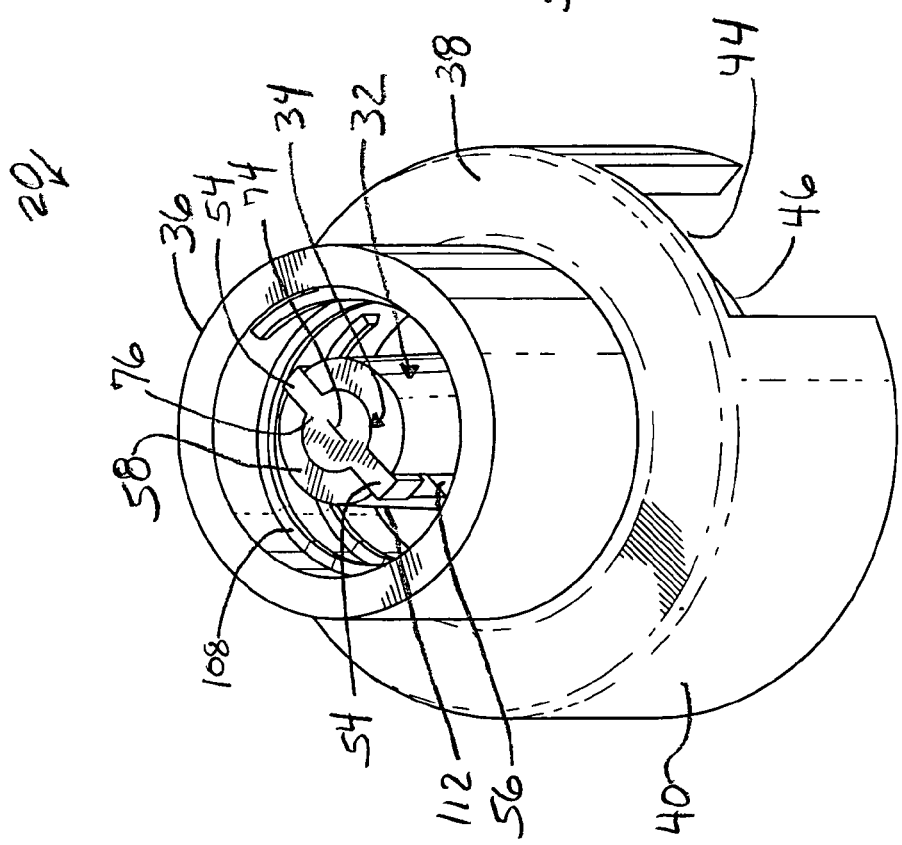
FIG. 5A
FIG. 5

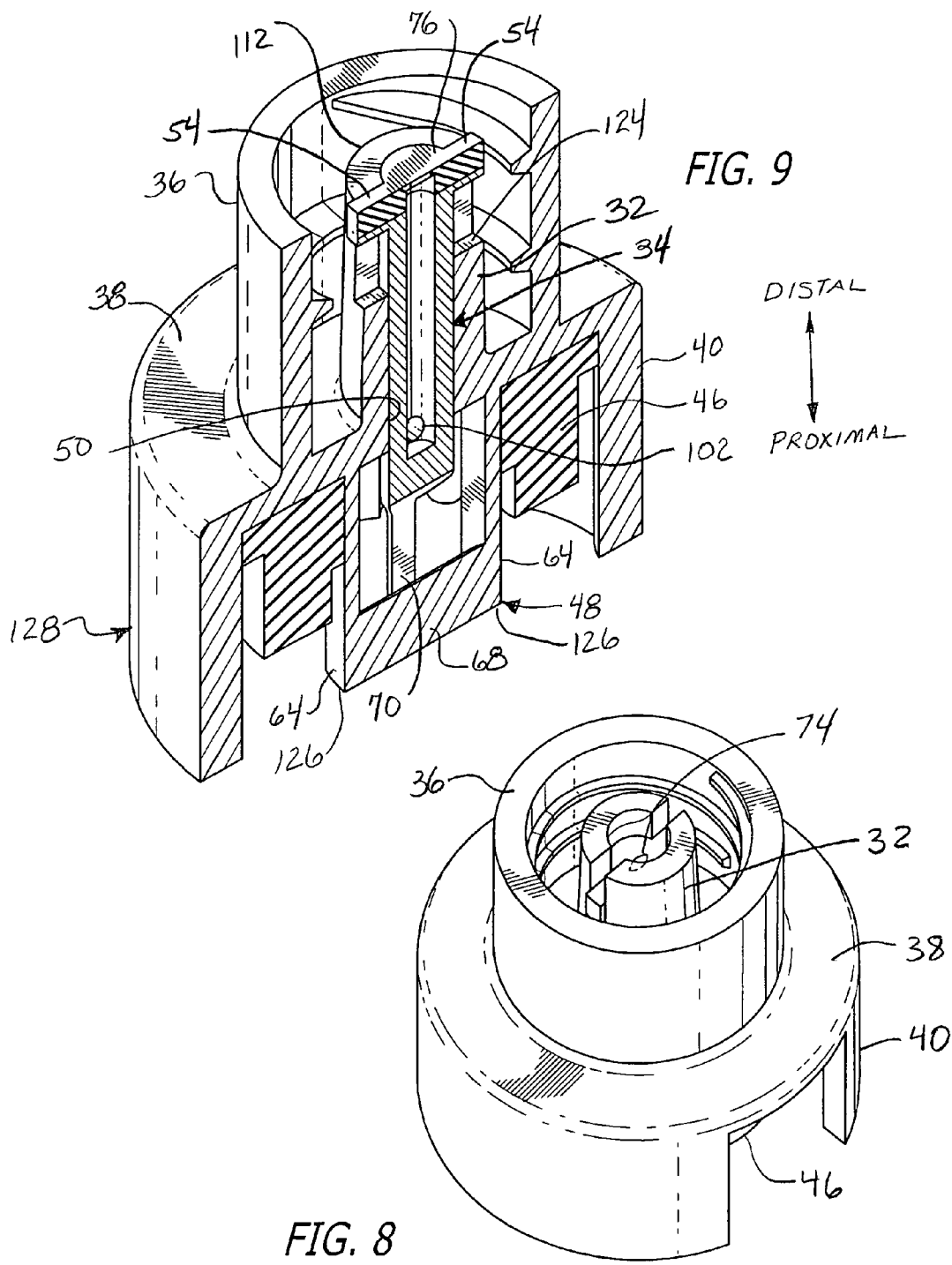

NEEDLE FREE BLOOD COLLECTION DEVICE WITH MALE CONNECTOR VALVE

BACKGROUND OF THE INVENTION

The present invention generally relates to blood collection devices and more specifically to self-sealing, needle free blood collection devices.

Collecting blood from a patient, though a necessary and routine medical procedure, is often a difficult task, particularly in the case of children, small adults, and the elderly, who may have small or "rolling" veins. As a result, multiple needle punctures of the patient may be required to obtain proper access to a vein, causing distress to both the patient and the caregiver. Worse, this procedure may have to be repeated several times over the course of the patient's hospital stay to draw blood samples for prescribed tests or on-going patient monitoring.

To get blood from the patient into a vial, the conventional method is to employ a device that combines a needle holder with a blood collection vial. This device typically has a double-ended sharpened cannula with one sharpened end being unprotected for insertion into a vein of the patient's arm and the opposite, second, sharpened end being located within a flange used to receive a sealed blood vial. As the blood vial is pressed into the flange, the second sharpened end of the cannula pierces the blood vial's septum to initiate the flow of blood from the patient into the vial for collection. While this approach may be satisfactory for single-puncture applications where a one-time withdrawal or administration of fluids is to occur, the double-ended cannula and cannula holder device are not well-suited for multiple or long-term uses. Manipulation of the device when exchanging vials can be painful to a patient, and when one vial is disconnected so that another can replace it, the patient's blood may flow out the cannula in the meantime, causing contamination.

In order to address some of these concerns, as is now known and widely practiced in the art, an intravenous (referred to as "I.V.") tubing set including a venipuncture needle (sharpened cannula), a length of plastic tubing extending from the needle, and a solution bag at the opposite end of the tubing have been used. The tubing may also include one or more valve ports along its length for access to the I.V. line. In use, the venipuncture needle is inserted into a patient's vein, just as with the typical blood collection device. However, once the I.V. line is placed in connection with the venipuncture needle, the needle can remain in position long-term, allowing blood to be withdrawn and medicines and other solutions to be administered intravenously on multiple occasions without having to repeatedly puncture the patient. In employing the typical I.V. tubing set, blood is often collected in the solution bag attached to the tubing or in a vacuumized blood collection vial through a valve port positioned along the tubing. Blood collection vials are typically manufactured with a partial vacuum within the vial and are sealed with a puncturable membrane that functions to maintain the partial vacuum within the vial yet allow access to the vial to collect blood. When the sealing membrane is punctured, the vial draws the patient's blood into the vial due to its partial vacuum. Because of the partial vacuum manufactured into blood collection vials, they are often referred to as being "vacuumized."

Prior art valve ports often entail conventional female connectors so that extension sets or gas sampling lines, syringes, or other such medical devices can be connected to a patient's I.V. line. The conventional female connector is open or unsealed, so that upon disconnection of the medical device, any residual fluids within the connector could come into contact with the patient or caregiver, risking contamination. Because of this risk, self-sealing, needle-free female luer connectors have been developed and employed in the art such that, upon disconnection, the female connector seals itself and traps any residual fluids within the patient's I.V. line.

Where a venipuncture needle and tube are employed and blood is to be withdrawn through a valve port in the patient's I.V. line into a blood collection vial, the conventional double-ended needle cannula holders have still been employed to facilitate the transfer of blood through the valve port and into the vial. One of the valve ports in the patient's I.V. line may be configured with a pierceable septum so that the free end of the sharpened cannula can be inserted into the valve port through the septum, rather than directly into the patient, and the holder at the opposite end of the cannula can accept a blood collection vial as before. However, this method, though effective, is not as desirable because the use of the sharpened cannula for insertion into the valve port presents opportunities for inadvertent needle punctures and resulting contamination of the caregiver and patient.

Alternatively, because I.V. line valve ports may now also be configured with self-sealing female luer connectors, vial holders known in the art may be utilized having a single sharpened cannula extending within the holder for acceptance of the vial, while the opposite end is generally configured as a conventional open male connector (with no valve) for interfacing the female connector on the I.V. line. In this way, needle-free connection between the vial holder and the patient's I.V. line is achieved. However, because the male connector is open and unsealed, any residual blood in or about the connector will be exposed when the holder is disconnected from the I.V. female connector valve port after use. Further, the single-needle cannula, though shielded by the vial holder and the required piercing of the vial septum by the cannula still pose a risk of an inadvertent needle puncture or cross-contamination. Relatedly, the required handling of the vials, including the removal of a full vial and the replacement of an empty vial in the holder, may pose additional risks that could be avoided if the vial and holder were an integral, self-sealing blood collection unit.

Therefore, those skilled in the art have recognized a need for a needle free blood collection device that includes a self-sealing male luer connector that may be connected to a female luer connector for the safe and effective collection of blood without the risks associated with the use of sharpened needles and changing vials in a holder. Further, those skilled in the art have recognized a need for a self-sealing male luer connector that may be connected to a female luer connector that forms a part of a patient's I.V. line. Even further, there has been recognized a need for an integral self-sealing male luer connector with a blood collection vial under partial vacuum such that a blood sample may be taken with the integral device and that device may then be disconnected from a female connector and forwarded for analysis. The present invention fulfills these needs and others.

SUMMARY OF THE INVENTION

Briefly and in general terms, the present invention is directed to a needle free vacuumized blood collection device for collecting blood from a patient in a vial through a needle free male connector having a valve. Mounted within an internal bore of the male connector is a valve element that opens or closes a flow passage to the blood collection vial. A spring device biases the valve element in the distal direction to a closed, or non-flow, configuration. Upon connection of the male connector to a female connector having a blunt or flat front surface, the valve element is automatically shifted to the flow configuration so that blood from the patient is collected in the vial. The valve element includes an activation arm extending outward from the male connector to contact the female connector device to shift the valve element to the flow configuration.

In further aspects, the activation arm of the valve element is configured to extend radially outwardly from the distal end of the valve element beyond the outside surface of the body of the male connector to engage the female connector upon insertion of the male connector of the blood collection device therein. As such, the activation arm cooperates with the proximal movement of the female connector during connection to shift the valve element proximally, thereby activating the device and allowing for fluid flow through the flow opening in the distal end of the valve element and the flow passage in the central post and into the collection vial. In another aspect, two substantially opposite activation arms exist on the valve element and two corresponding lateral openings or notches are formed in the tubular male connector so as to accommodate the axial movement of the valve element.

In more detailed aspects in accordance with the invention, to form the activation arms, opposite radially-outwardly extending tabs may be formed integral with the valve element's tube onto which a resilient end cap is mounted. As a result, the activation arms have the required stiffness to transmit the activation forces to the valve element to activate the device, while the distally-facing surfaces of the arms are made of a flexible, conforming material that serves to seal the activation arms within the notches and prevent leakage around the distal end of the valve element.

In yet further detailed aspects, the male connector is formed as part of a body member, which includes a body flange projecting in the proximal direction. The body member flange is configured to receive the open end of the collection vial. The body member flange may be formed with lengthwise, spaced-part, radially-inwardly extending ribs configured to engage the vial and removably secure the vial in place within the body member flange. A stopper is mounted, such as by press-fit, within the body member flange to provide a sealing mounting cavity for the vacuumized vial.

In another aspect, the body member includes a spring support at its proximal end to provide a mounting for a spring device so that the biasing forces of the spring device will be directed in the distal direction to close the valve element. In one case, the support device comprises a pair of brackets between which a spreader bar is mounted. In another aspect in accordance with the invention, the spring device includes two spaced-apart spring legs formed at the proximal end of the valve tube that straddle the spreader bar. The width of the spreader bar is selected to force the spring legs apart thus storing mechanical energy in the legs resulting in the spring device being biased in the distal direction. In a more detailed aspect, the shape of the spreader bar is in a rounded wedge so that further proximal movement of the spring device causes the development of increased mechanical biasing forces in the distal direction.

In another detailed aspect, the valve element includes an elliptically-shaped flow opening that is forced closed by a smaller diameter bore in the distal tip of the male connector when the valve element is forced to the distal direction. In another detailed aspect, the spring device is configured so that it provides constant biasing force against the valve element in the distal direction even when the valve element is in the non-flow configuration.

In yet a further detailed aspect, the valve tube includes a lateral opening at its proximal end to form part of the flow passage through the valve element. The stopper includes a counterbore that is small enough so that when the lateral opening of the valve tube is within the counterbore, the counterbore seals the lateral opening.

These and other features and advantages of the present invention will become apparent from the following detailed description of the preferred embodiments which, taken in conjunction with the accompanying drawings, illustrate by way of example the principles of the invention.

BRIEF DESCRIPTION OF THE DRAWINGS

FIG. 5 is an enlarged top perspective view of the male connector and valve element of the blood collection device shown in FIG. 2 showing the threaded collar in more detail and the body member flange within which a vial is mounted;

FIG. 5A presents a top view of the male connector of FIG. 5 showing the extension of the activation arms of the valve element outward from the male tip for interaction with the female connector to thereby place the valve element in the flow configuration;

FIG. 8 is an enlarged top perspective view of the blood collection device shown in FIG. 5 rotated somewhat with the valve element activated and in the flow configuration;

FIG. 9 is an enlarged, cross-sectional, perspective view of the blood collection device shown in FIG. 2 with the collection vial removed for simplicity and the view rotated by approximately ninety degrees with the valve element in the non-flow configuration;

DETAILED DESCRIPTION OF THE PREFERRED EMBODIMENTS

Figure 1:
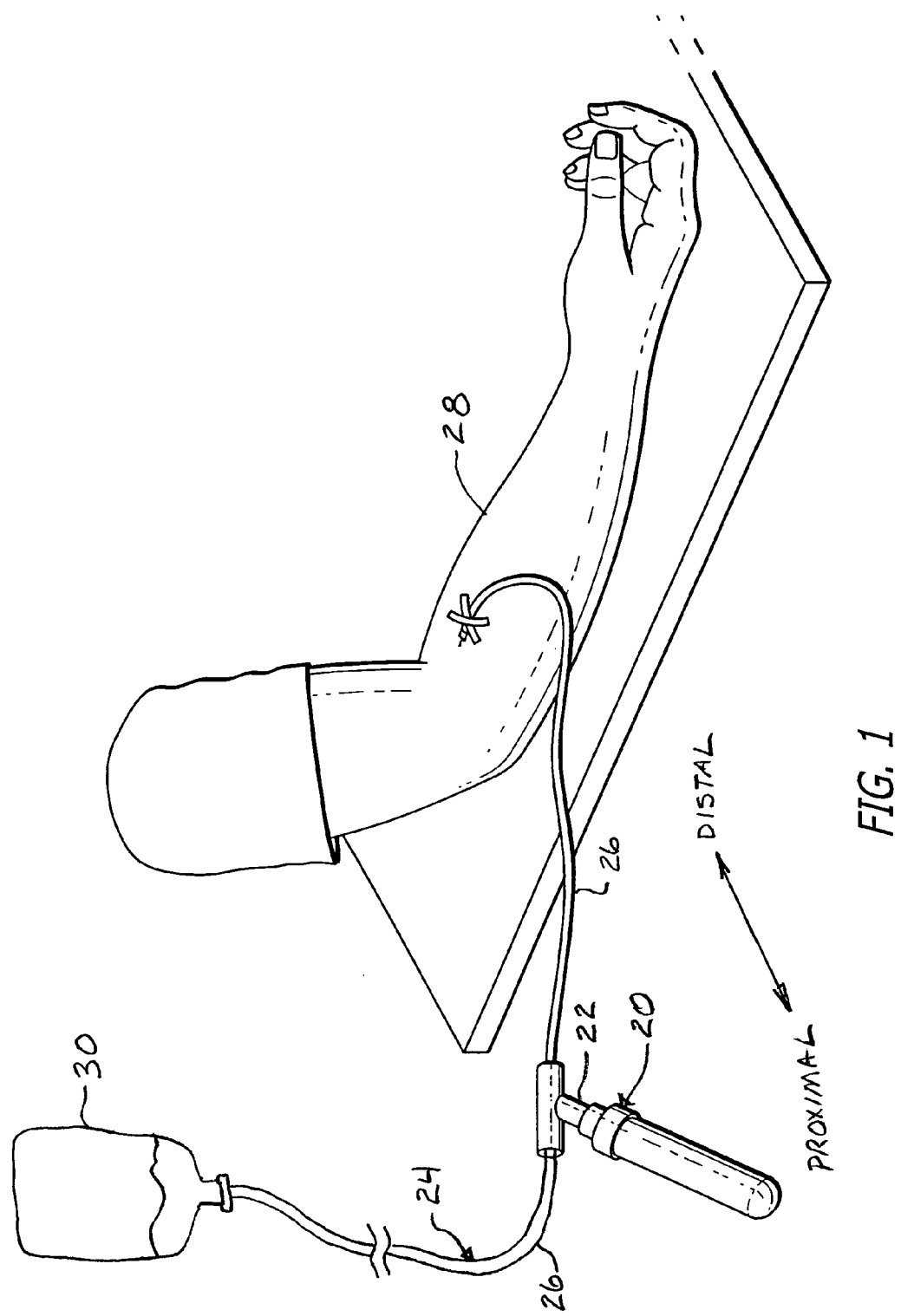
FIG. 1 is a simplified pictorial illustration of a patient I.V. administration set in connection with an exemplary embodiment of a needle free vacuumized blood collection device in accordance with aspects of the present invention in which the blood collection device is connected to the patient's I.V. line for collection of a blood sample.

Referring now in more detail to the drawings for purposes of illustration, wherein like reference numerals designate corresponding or like elements among the several views, there is shown in FIG. 1 a needle free blood collection device 20 in accordance with aspects of the present invention operably connected to the proximal end of a female luer connector 22 that forms a part of a patient I.V. fluid administration set 24. The patient I.V. set 24 is presently used for the collection of blood through the I.V. line 26 that forms a part of the administration set 24. As is well known to those skilled in the art, I.V. fluid administration sets are used to interconnect a source of fluid such as the medical fluid bag 30 with the patient 28 for whom the fluid has been prescribed. In another case, the I.V. bag may be used to collect the patient's blood. A clamp or clamps not shown may be used on the tube 26 of the I.V. line as needed to isolate the bag from points downstream in the I.V. line.

As a matter of reference only, the term "distal" is meant to refer to the direction toward the patient 28 and "proximal" is meant to refer to the direction away from the patient, or toward the collection device 20 or dispensing device such as the solution bag 30 shown. Also, "downstream" is meant to refer to the direction of the patient while "upstream" is meant to refer to the direction of the solution bag 30.

Figure 2:
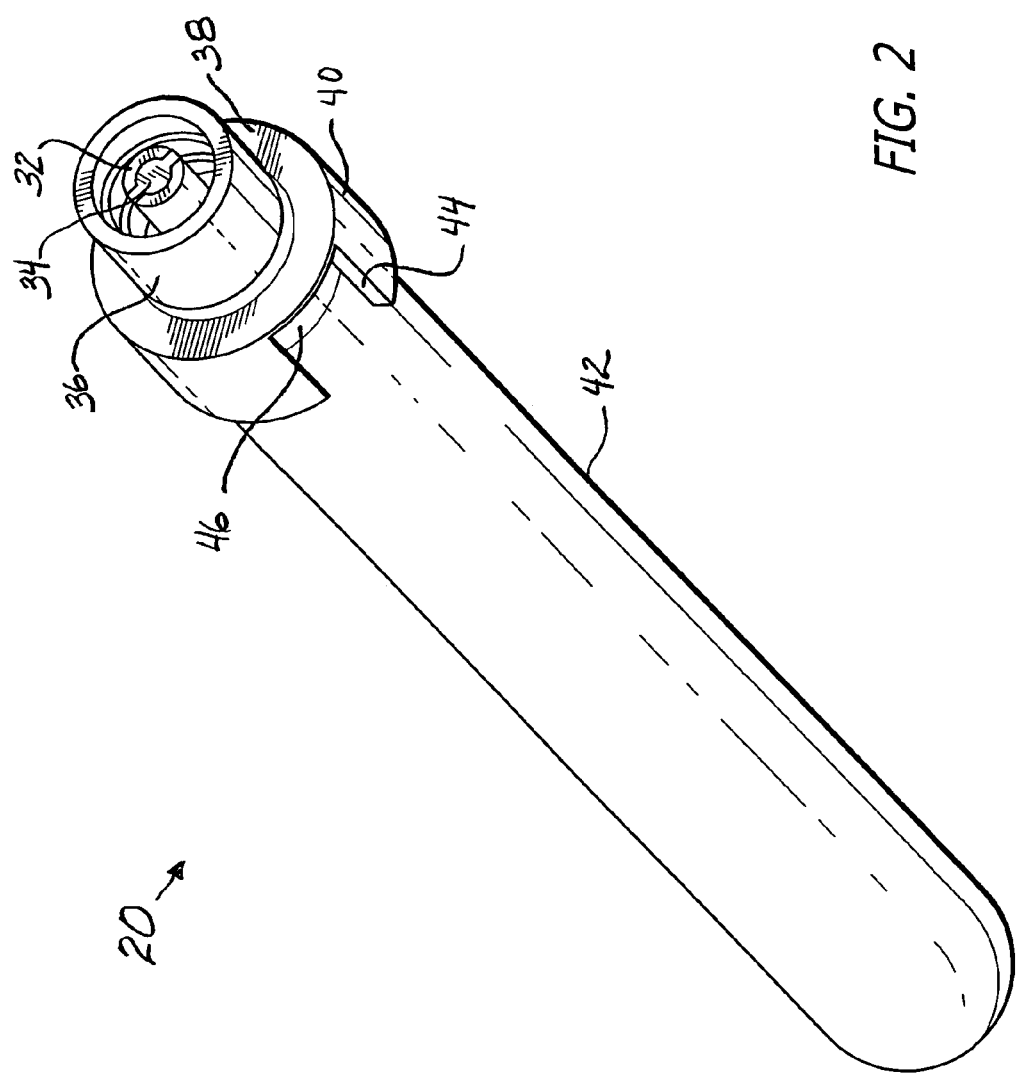
FIG. 2 is a perspective view of an exemplary embodiment of a needle free vacuumized blood collection device in accordance with aspects of the present invention disconnected from the patient's I.V. line of FIG. 1 so that the male connector, the valve element, and the collection vial can be seen more clearly.

Referring now to FIG. 2, there is shown an enlarged perspective view of one embodiment of the blood collection device 20 of FIG. 1. The blood collection device comprises a male connector 32 having an internal valve element 34. The male connector in this case is generally configured as a conventional ANSI/AAMI/ISO male luer connector for taper-to-taper connection with a complementary female luer connector, such as that shown in FIG. 1. The male connector is surrounded by a threaded collar 36 for engaging the threads of a female connector. The male connector is engaged through a body member 38 with a body flange 40 to which is mounted a blood collection vial 42. In this case, the interior of the vial is under a partial vacuum to assist in the collection of a patient's blood. The flange includes gaps 44, one of which is shown, to assist in mounting a vial. A portion of a stopper 46 can also be seen that assists in mounting the vacuumized vial to the body member.

Figure 3:
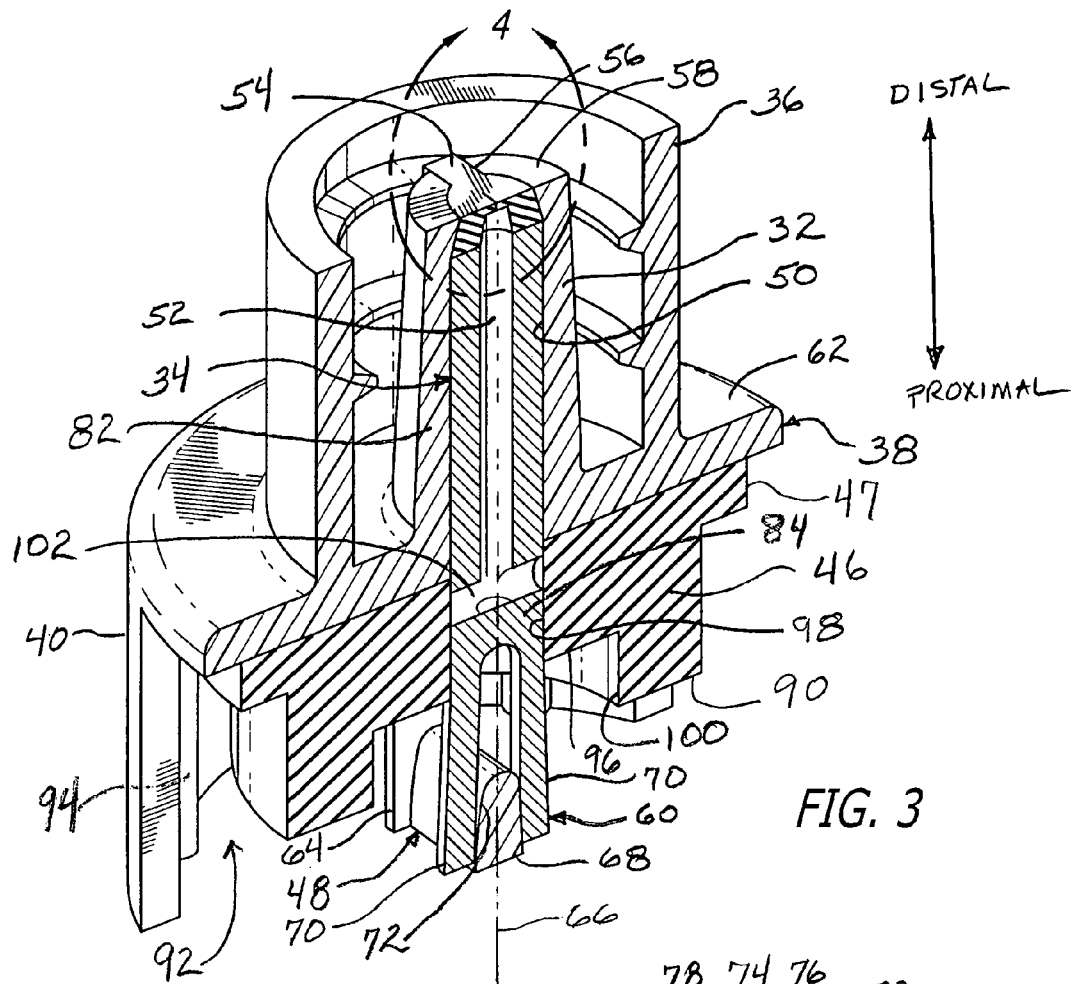
FIG. 3 is an enlarged, cross-sectional, perspective view of the male connector and valve element shown in FIG. 2 with the collection vial removed for clarity of illustration of the spring device that biases the valve element to the closed position.

Referring now to FIG. 3, there is shown an enlarged, cross-sectional, perspective view of the male connector 32 of FIG. 2. The male connector is formed as part of the body member 38 in this embodiment and is hollow. The male connector extends distally from the body member while a spring support 48 extends proximally. The internal bore 50 of the hollow, tubular male connector is configured for slidable receipt of the valve element 34 so that a flow passage 52 formed in the valve element may be selectively opened and closed. When the valve element is opened, flow into the vial 42 (FIG. 2) may occur but when closed, flow into the vial is prevented.

In the embodiment of FIG. 3, the valve element 34 has been formed with two oppositely extending activation arms 54 (one of which is shown) at its distal end 58 that extend radially outwardly through lateral openings 56 in the distal tip of the male connector 32. The activation arms extend far enough outward from the male connector to engage a standard luer female connector 22 (FIG. 1) as it is engaged with the male connector. Upon engagement, and upon further movement of the male and female connectors together, the activation arms and the valve element are shifted in the proximal direction to open the flow passage 52 and permit flow into the vial. A spring device 60 biases the valve element toward the distal direction to the "non-flow" configuration shown in FIG. 3 to prevent flow into the vial and flow out of the vial. The spring device engages the spring support 48 that provides support for the biasing forces of the spring device toward the distal direction. The spring device is configured to provide enough biasing force to move the valve element 34 in the bore 50 of the male connector 32 to seal the flow passage 52. This prevents the loss of the partial vacuum existing within the vial before use and the escape of blood collected in the vial after use.

In the non-flow configuration shown in FIG. 3, the valve element 34 is closed so that flow through the collection device 20 is prevented.

With continued reference to FIG. 3, as discussed above, the male connector 32 has an exterior surface tapered from a larger diameter in the proximal direction to a smaller diameter in the distal direction in accordance with ANSI/AAMI/ISO standards for engaging a conventional female luer connector having a tubular barrel with a complementary tapered interior surface. Further, the body member 38 has a distally-projecting thread collar 36 disposed circumferentially about the male connector for threadable receipt of the female connector's tubular barrel with threads to secure the interconnection of the female and male connectors during use. The male connector and the threaded collar both project from a perpendicular planar wall 62 of the body member which has a generally annular perimeter in this embodiment that forms the base of the male connector.

Projecting in the proximal direction from the planar wall of the body member is the spring support 48. The spring support has two brackets 64 extending in the proximal direction, one of which is shown in FIG. 3. The two brackets are spaced apart from each other and each is offset from the longitudinal axis 66 of the male connector so as to not interfere with the axial movement of the valve element 34 within the central internal bore 50. A spreader bar 68 connects the two brackets of the spring support 48 so as to extend beneath the internal bore 50 to engage the spring device 60. The combination of the brackets and spreader bar acts to support the spring device so that the bias it develops will be directed in the distal direction.

Turning now to the spring device 60, in one embodiment the spring device is formed at the proximal end of the valve element 34 and is configured as a pair of proximally-extending spring legs 70 so as to straddle the spreader bar 68. The spring legs may be configured to have a distance between them that is smaller than the transverse width of the spreader bar. When the valve element is moved in the proximal direction, the spring legs are forced to flex outwardly as they pass over the spreader bar thereby developing and storing bias energy. In the embodiments shown herein, even in the rest or "non-flow" configuration shown in FIG. 3, the spring legs are flexed outwardly thereby storing bias energy to keep the valve element in the non-flow configuration shown. Because the spring legs will attempt to release this stored energy by shifting back toward their natural, at-rest, non-flexed positions, the spring legs will effectively serve to push or bias the valve element in the distal direction within the internal bore 50.

To further facilitate the storage of energy in the spring legs 70 for biasing the valve element 34 is the distal direction, the spreader bar 68 may be formed with tapered side surfaces 72. In the embodiment shown in FIG. 3, the spreader bar would be wider in the proximal direction than in the distal direction thus spreading the spring legs farther apart as the valve element is moved in the proximal direction. As a result, the outward flex of the spring legs is increased as the valve element travels proximally within the bore, thereby increasing the amount of potential energy stored in the spring legs to bias the valve element in the distal direction. This increase in stored energy will further enable the valve element to overcome any inherent starting friction and insure that the valve element will fully return to the distal end of the internal bore 50. This same effect could be achieved by distally tapering the inside edges of the spring legs, rather than the outside surfaces of the spreader. A variety of other spring devices, and accordingly, a variety of spring support configurations may be possible for incorporation in the present blood collection device without departing from the scope of the invention.

Figure 4:
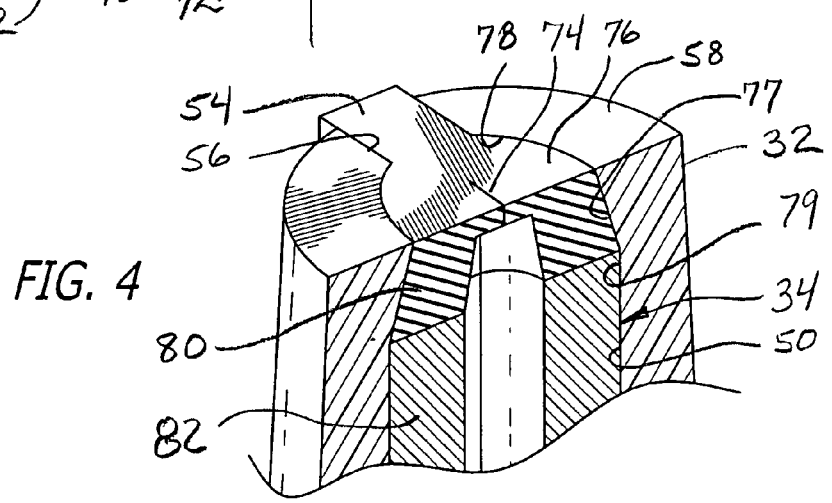
FIG. 4 is an enlarged, cross-sectional, perspective view of the tip of the male connector shown in FIG. 2 with the valve element and its flow opening shown more clearly.

Referring now to FIG. 4, there is shown an enlarged partial cutaway perspective view of the distal tip 58 of the male connector 32 with the valve element 34 at its most distal position in its non-flow configuration. As can be seen in this enlarged view, the valve element includes an opening 74 in its distal end 76, although it is squeezed shut in this non-flow configuration. It will also be noted that a distal tip 58 of the male connector includes a tapered internal bore 77 in which the bore has a larger diameter in the more proximal position to a smaller diameter 78 at the distal tip. At that smaller diameter location 78, the valve element is compressed radially which causes closure of the opening 74. In order for this compression of the valve element and closure of the opening to occur, the valve element comprises a resilient distal end component 80. In this case it is a resilient end cap 80. It can also be seen from FIG. 4 that the activation arms 54, one of which is visible, are formed of the end cap and are thus resilient.

In order to obtain the necessary resiliency for radial compression at the distal end yet have column strength to move longitudinally along the male connector bore 50, the valve element 34 can be formed from a rigid or semi-rigid central valve tube 82 having the flexible end cap 80 disposed at its distal end 76. The end cap is configured having an at-rest outside dimension substantially equivalent to the larger inside diameter 79 of the bore of the male connector so as to effectively seal the distal end of the valve element within the bore along its length. When the valve element is shifted distally within the bore so that the end cap is within the distally tapered portion 77 of the bore, which has a smaller diameter than the natural at-rest outer diameter of the end cap, the end cap is then compressed radially inwardly. As such, the flow opening 74 formed in the end cap, which is naturally in an open configuration, is closed due to the distal movement of the valve element and the corresponding compression of the end cap within the distally tapered position of the bore. In this way, the distal end 58 of internal bore is completely sealed by the end cap when the valve element is in its distally-biased position, and no fluid flow is allowed in or out of the blood collection device when it is disconnected before and after use. It can also be noted that the distal surface 76 of the end cap is substantially flush with the distal end 58 of the male connector and is thereby accessible for contact or surface sterilization.

Referring further to FIG. 3, the male connector 32 is formed with the proximally-projecting body member flange 40 extending from the annular perimeter of the planar wall or base 62. In one embodiment, the stopper 46 is disposed within the body member flange and substantially about the proximally-projecting spring support 48. The outer diameter 47 of the stopper is slightly larger than the inside diameter of the body member flange so that the stopper will have a "press fit" within the body member flange and will be held in place because of this size difference. A central portion 90 of the stopper, having an outside diameter smaller than the inside diameter of the body member flange, extends in the proximal direction so as to form a proximally-facing annular cavity 92 between the central portion and the body member flange for receipt of the open distal end of the collection vial 42. In one embodiment, the outside diameter of the central portion is large enough so that a sealing, interference fit is achieved with the inside surface of the vial. The outside surface of the vial is captured by the body member flange through a number of assembly means, including but not limited to horizontal or vertical ribs 94, a frictional interference fit, solvent bonding, or ultrasonic welding, or other.

However, in another embodiment, it may be desirable to removably mount the male connector 32 onto the vial 42 so as to be able to selectively access the vial's contents by completely removing the connector. As such, in the embodiment shown, the spaced-apart, lengthwise, inwardly projecting ribs 94 are formed about the interior surface of the body member flange so as to frictionally engage the outside surface of the vial and removably secure the vial in place within the body member flange, with the seal of the vial being maintained on its inside surface by the stopper.

Referring still to FIG. 3, the stopper 46 is further formed with a central counterbored hole 96 with distal and proximal hole portions 98 and 100 so as to accommodate the axial movement of the valve element 34 within the internal bore 50. The diameter of the distal hole portion 98 is substantially equivalent to that of the internal bore so that the distal hole is effectively a continuation of the internal bore. The proximal hole portion 100 has a diameter greater than the distal hole portion so as to create clearance for the outward flex of the spring legs 70 and for blood flow through the flow passage 52 as the valve element is shifted in the proximal direction, as explained in more detail below.

In one embodiment, the valve element 34 includes a lateral hole 102 located substantially at the proximal end of the valve element that interconnects with a longitudinal hole 52 disposed along the axis 66 of the valve element. Together, the lateral hole, the longitudinal hole, and the opening 74 through the end cap 80 form the flow passage 52. In the embodiment shown in FIG. 3 and other figures, the lateral hole 102 is actually a cross hole extending completely through the valve tube 82. The valve tube may actually have more lateral holes, or only one, depending on the embodiment. The length of the valve tube and the location of the lateral hole at its proximal end are selected so that the lateral hole is positioned within the stopper 46 when the valve element is in the non-flow configuration shown in FIG. 3. The stopper seals the lateral hole when in the non-flow configuration. In this way, any partial vacuum within the collection vial 42 (FIG. 2) will be maintained while the blood collection device 20 is in a non use status. Thus there are two seals: the opening 74 at the distal end 76 of the valve element will be squeezed shut due to the radial compression applied by the male connector 32; and the lateral hole at the proximal end 84 of the valve element will be sealed shut by the distal portion 98 of the counterbore 96 of the stopper. The above shows only exemplary embodiments. It should be appreciated that other configurations of sealingly installing the male connector on the collection vial may be employed without departing from the scope of the invention. For example, the outside of the distal end of the vial may be sealingly installed within the body member flange and the lateral hole may be configured along the valve element so as to be sealed by the internal surface of the bore 50 of the male connector when the valve element is located in the non-flow configuration, so as to effectively eliminate the stopper while still providing for the maintenance of the vial's initial partial vacuum.

Turning now to FIG. 5, there is shown an enlarged perspective view of the distal end 58 of the male connector 32 showing in more detail the threaded collar 36, the body member 38, the body member flange 40, and the distal end 76 of the valve element 34. The threaded collar is positioned coaxially about the tubular male connector and provides internal threads 108 that will engage the external threads on a female Luer connector to lock the male and female connectors together once engaged. In this embodiment, the threaded collar is fixed in position in relation to the body member; however, a freely rotating threaded collar may also be used. Further in this embodiment, the body member flange 40 is formed with one or more circumferential gaps 44 about its perimeter. These gaps facilitate the assembly and disassembly of the collection vial 42 (FIG. 2) within the body member flange by allowing access to the distal edge of the vial and enabling the body member flange to flex slightly radially outwardly so as to snap or press the vial within the proximally-facing annular cavity 92 formed between the body member flange and the stopper 46.

As also shown in FIG. 5, the valve element 34 includes two radially outwardly extending activation arms 54 that extend beyond the outside surface 112 of the tubular body. In the embodiment shown, the activation arms are substantially opposite one another so as to provide for symmetrical engagement with a female connector, but it should be appreciated that other numbers and arrangements of activation arms may be employed and still be within the scope of the present invention. The lateral openings or notches 56 are formed in the male connector 32 to accommodate the respective activation arms and allow for their axial movement along with the valve element 34 itself. By extending beyond the circumference of the male body, the activation arms will engage the female connector's proximally-facing edge as the female connector is brought into contact with the male connector of the blood collection device to make the connection. Thus, any further movement of the female connector in the proximal direction, as when the female connector is threaded onto the male connector, will shift the valve element in the proximal direction by way of the activation arms.

FIG. 5A presents a top view of the male connector 32, threaded collar 36, and body member 38 showing that the activation arms 54 extend beyond the outer surface 112 of the male connector. The length of such extension would be dependent on the tolerances between male and female luer connectors and the amount of depth desired for coupling with the female luer connector. More specifically, the valve element must be moved by a certain distance before the distal opening 74 will open and before the proximal lateral hole 102 (FIG. 3) becomes unsealed. Similarly, if the male connector 32 is to mate with a female connector having an internal valve, that female valve may not open unless the female connector engages the male connector by a certain distance. The length that the activation arms extend beyond the outer surface of the male connector depends on these factors and is selected accordingly. In one embodiment, the activation arms extended beyond the outer surface of the male connector by one mm.

Figure 6:
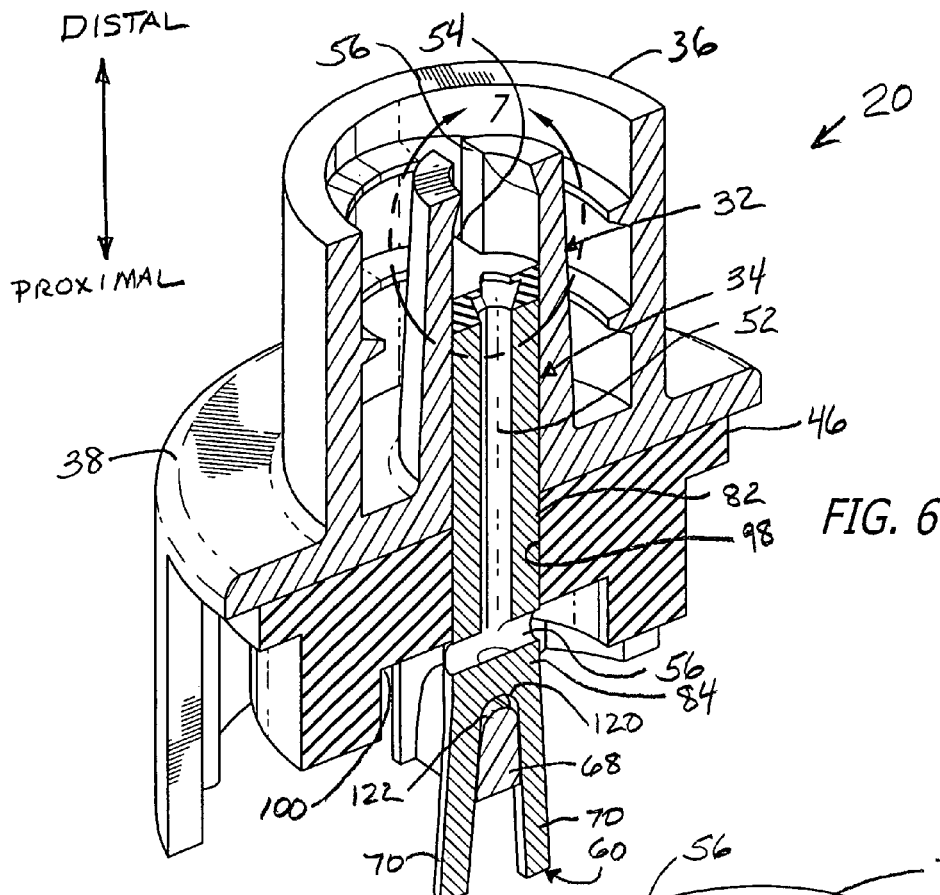
FIG. 6 is an enlarged, cross-sectional, perspective view of the blood collection device shown in FIG. 3 showing the configuration of the valve element and spring device when the valve element is in the flow configuration due to engagement with a female connector.

FIG. 6 presents an enlarged cross-sectional perspective view of the blood collection device 20 of FIG. 5 rotated ninety degrees with the valve element 34 now activated through engagement of the male connector 32 with a conventional female luer connector, which is not shown so as to preserve clarity of illustration of the embodiment of the present invention. When the valve element is shifted in the proximal direction as shown, the two proximally-projecting spring legs 70 forming the spring device 60 are forced to flex outwardly as they are pushed in the proximal direction and must further straddle the spreader bar 68. Before the crotch 120 formed between the spring legs reaches the distal surface 122 of the spreader, the activation arms 54 (part of one being shown) will engage stop surfaces 124 (shown in FIG. 5) formed at the bottom of the lateral openings 56 so as to prevent any further proximal movement of the valve element.

With continued reference to FIG. 6, the flow passage 52 through the valve element 34 is again shown and terminates in the cross-hole 56 at the proximal end 84 of the valve tube 82. As discussed above, the cross-hole is positioned along the valve tube so as to be located within the relatively larger proximal hole portion 100 in the stopper 46 when the valve element is in its proximal-most position, as shown in FIG. 6. In this way, the cross-hole is no longer sealed within the relatively smaller distal hole portion 98 of the stopper, but is exposed to allow flow into the vial 42 (FIG. 2).

Figure 7:
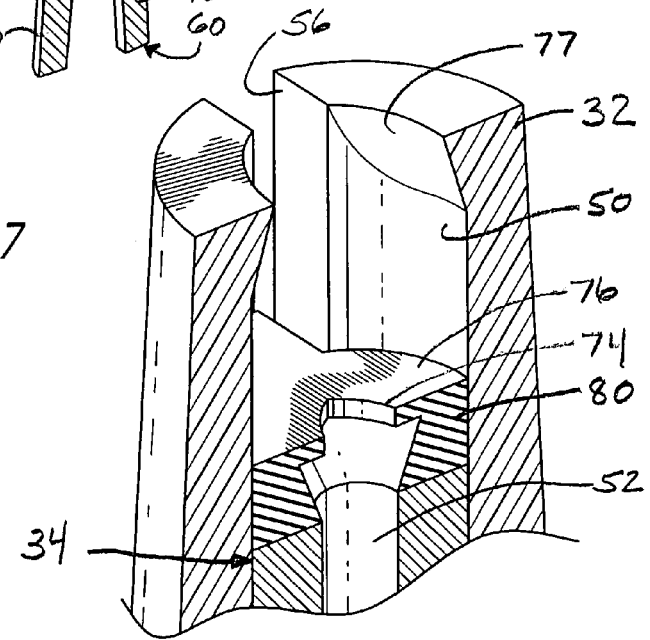
FIG. 7 is an enlarged, cross-sectional, perspective view of the male connector tip and valve element of FIG. 6 showing more detail of the configuration of the elements when the valve element is in the flow configuration.

Referring now briefly to FIG. 7, there is shown an enlarged, cross-sectional, perspective view of the male connector 32 of FIG. 6 showing the distal end 76 of the valve element 34 shifted in the proximal direction within the internal bore 50. In this position, the end cap 80 is now positioned proximal to the distally tapered portion 77 of the internal bore so as to no longer be radially compressed and is now expanded outward to its natural at-rest configuration within the relatively larger main bore with the opening 74 now open for flow in the flow configuration. As such, when the blood collection device of the present invention is connected to a female luer connector so as to activate the valve element, a complete flow path is then formed from the female connector through the flow opening in the distal end cap of the valve element, through the through-hole 67 and the cross-hole 68 making up the flow passage, and then into the blood collection vial.

Because of the non-flow configuration of the device 20 shown in FIG. 5 and the flow configuration shown in FIG. 6 caused by movement of the valve element 34, the initial partial vacuum within the vial is maintained when in the non-flow configuration and is applied to the patient for blood collection in the flow configuration. This partial vacuum acts to efficiently pull the patient's blood into the vial for the quick and convenient collection of the sample. In this regard, it will be further appreciated that the flexibility of the end cap serves to also seal the end cap within both the internal bore itself and within the lateral notches 56 so that fluid can only pass through the flow passage 52.

With further reference to FIG. 7 and to the top perspective view of the male connector 32 shown in FIG. 8, the flow opening 74 formed in the end cap 80 is shown as being substantially elliptical in shape when the cap is in its natural, uncompressed configuration, as when it would be when no forces are applied to it, such as when it is not mounted within the male connector 32. The end cap resumes this natural configuration with the flow opening 74 in the open configuration when the male connector 32 is connected to a female luer connector, as in FIG. 1. It will be appreciated that the shape of the opening 74 may also be referred to as a marquise shape, and that other shapes of an opening may be used, such as folded or pleated. Other opening shapes may be formed in the end cap so as to be selectively closed when the end cap operates in response to the distal movement of the valve element, without departing from the scope of the present invention.

Referring now to FIG. 9, there is shown an enlarged, cross-sectional, perspective view of the male connector 32 rotated ninety degrees from FIG. 5 and also in the non-flow configuration. As best shown in this view, the opposite radially-outwardly extending activation arms 54 may be formed at the distal end of the valve element 76 so as to create somewhat of a "T" cross-section shape. As also shown and explained above, because the outer surface 112 of the male connector is configured to engage the inner tapered surface of a conventional female luer connector and the activation arms extend radially beyond the male body's outer surface, it will be appreciated that as the female connector is advanced in the proximal direction so as to connect to the male connector, the proximal edge of the female connector will be brought into engagement with the activation arms. Then, further proximal movement of the female connector into engagement with the male connector will shift the valve element in the proximal direction to allow blood flow into the vial (not shown). The bottom edges of the lateral slots 56 in which the activation arms travel serve as stops 124 to prevent over-travel of the valve element.

With continued reference to FIG. 9, the spring support 48 is shown as including two brackets 64 positioned adjacent the central bore 50 to not interfere with the axial movement of the valve element 34 therein. The spreader bar 68 about which the spring device legs 70 straddle to flexibly bias the valve element to the distal direction is configured to span the distance between the proximal ends 126 of the brackets.

As shown, the blood collection device 20 in these embodiments is configured so as to integrally include the distally projecting male connector 32, the circumferential threaded collar 36, the body member 38, the spring support brackets 64, and the annular body member flange 40. As such, it will be appreciated by those skilled in the art that these devices are well-suited for manufacture as an integrated single valve housing component 128 through an injection molding process. In this way, the housing 128 may be formed from a wide variety of medical grade plastics such as rigid or semi-rigid thermoplastics including, but not limited to, high density polyethylene, polypropylene, polycarbonate, ABS, acrylic, or any of the olefins. Similarly, the stopper 46 may also be formed from an injection or plug molding technique. Because in an embodiment the stopper is designed to be press fit into the male connector's body member flange 40 and to selectively seal off the valve element's cross-hole 102, it is preferred that the stopper be made of a flexible, conforming material such as silicone rubber, thermoplastic vulcanate, or thermoplastic elastomer. Once the stopper is formed in a separate molding operation, it may then be simply press-fit within the male connector's body member flange.

Figure 10:
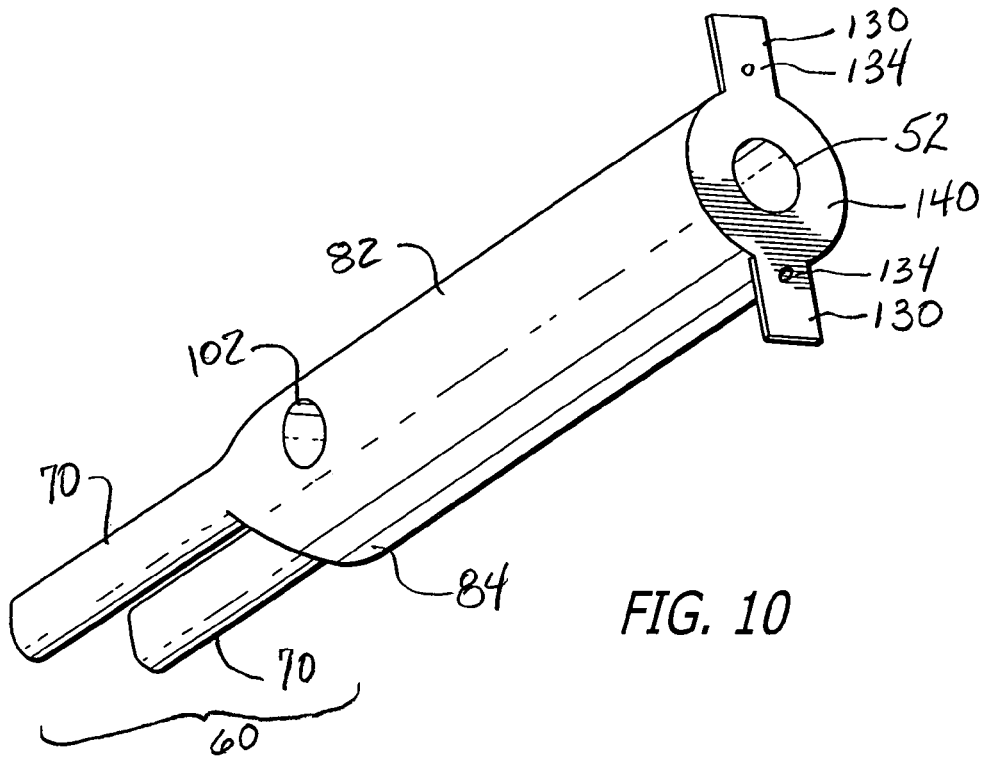
FIG. 10 is an enlarged perspective view of the more rigid valve tube of the valve element with the end cap removed so that detail of the post can be seen more clearly, and also showing an embodiment of a spring device located at the proximal end of the valve tube and formed as an integral part of the tube.
Figure 11:
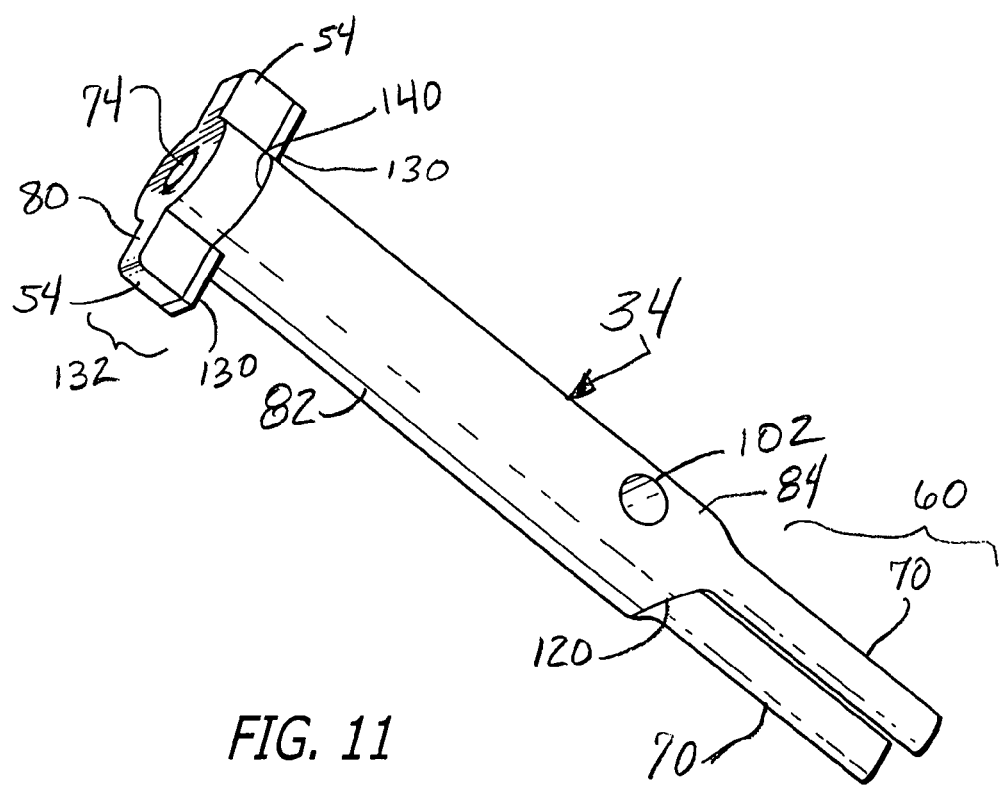
FIG. 11 is a perspective view of the valve element showing the valve tube having the end cap mounted at its distal end to form the complete valve element.

Referring now to FIGS. 10 and 11, there are shown perspective views of a partial and complete valve element 34 according to the one embodiment, so as to illustrate the construction and manufacture of the valve element. In FIG. 10 there is shown a relatively rigid valve tube 82 configured at its proximal end 84 with the cross-hole 102 and the proximally-projecting, spaced-apart spring legs 70 that form the spring device 60 for biasing the valve element in the distal direction within the internal bore of the male connector 32. At the distal end 140 there are formed radially-outwardly extending tabs 130 that form a proximal layer of the activation arms 54 so as to provide the arms with the needed structural integrity and stiffness to transmit the downward forces exerted by the female luer connector into proximal movement of the valve element upon connection to the male connector 32. It will be appreciated that the valve element tube 82 is also well-suited to an injection molding manufacturing process and, as such, may be made of any number of rigid and semi-rigid medical grade thermoplastics.

Referring again briefly to FIG. 4, in order to form the distally tapered portion 77 of the male connector's internal bore 50 in a molding process, it may be necessary to form an opening through the spreader bar 68 to accommodate the mold core pull (see FIG. 3 for the bar, although the core pull opening is not shown). In this case, the spring legs 70 of the valve element 34 that form its proximal spring device 60 may be configured with a wider stance so as to still engage the spreader bar.

Turning now to FIG. 11, there is shown a complete valve element 34 as would be installed in the blood collection device 20 in accordance with the present invention. The flexible end cap 80 has been disposed on the distal end 140 of the valve element tube 82 so as to sealingly cover the flow passage 52. As shown, the end cap is configured to cover the tabs 130 of the tube so as to form the distal layers 132 of the completed activation arms 54. It will be appreciated that the end cap may be formed from a variety of flexible, compressible materials such as silicone rubber, thermoplastic vulcanite, or thermoplastic elastomer in a separate molding operation and then be installed on the valve element tube in a secondary operation involving a bonding process or the like. As one alternative, the end cap may be over-molded directly onto the valve element tube in the same core in which the valve element itself was formed using techniques known in the art. To facilitate over-molding of the end cap onto the tabs at the distal end of the tube, each tab may be formed with one or more mounting holes 134 to allow the cap material to flow to both sides of the tabs and, once hardened or cured, secure the cap onto the post. In order to over-mold the cap onto the post and still form the internal geometry of the cap, a core pull must be made from the proximal end of the post, requiring that the flow passage 52 initially intersect the crotch 120 formed between the spring legs 70 and then be subsequently plugged through a back-filling molding process or through a separate secondary operation. The flow opening 74 of the end cap 80 may be formed as part of the molding process or in a secondary punch or cutting operation.

Still referring to FIG. 11, with the valve element 34 so formed, the distal layers 132 of the activation arms 54, like the entire end cap 80, are flexible and compressible. As such, as the end cap engages the proximal edge and even a portion of the interior surface of the female luer connector as it is engaged with the male connector 32, the activation arms will effectively seal within the lateral notches 56 and against the contacted surfaces of the female connector so as to prevent unwanted leakage around the end cap and only allow fluid flow through the flow opening 74 when activated.

In use, the blood collection device 20 in accordance with the present invention may be connected to a female luer connector 22 or other such connector that is part of a patient's I.V. administration set 24 (FIG. 1) so as to draw the patient's blood into the vial 42 for collection and subsequent testing. According to the principles of operation of the exemplary embodiment blood collection device, when the male connector 32 is in its at-rest position as shown in FIGS. 3-5A, the valve element 34 is in the non-flow configuration within the internal bore 50 so as to compress the flexible end cap 80 to close the flow opening 74. At the same time, with the valve element in its distal, non-flow, or closed position, the cross-hole 102 at the proximal end of the valve element is sealed within the counterbored distal hole 98 of the stopper 46 so as to further prevent flow through the valve element and to maintain the initial partial vacuum within the collection vial 42. Then, when a female connector 22 is engaged with the male connector 32, the proximal movement of the female connector causes the female connector to engage the activation arms 54 which shifts the valve element in the proximal direction accordingly to move the blood collection device to its flow, or activated, position as shown in FIGS. 6-8. In so doing, the flow passage 52 through the valve element is essentially opened at both ends to allow flow therethrough. At the distal end, the flow opening 74 is opened as the end cap expands to its uncompressed configuration within the larger inner diameter of the male connector bore 50, and at the proximal end, the cross-hole 102 exiting the stopper 98 so as to be exposed to the partial vacuum in the vial 42. In this flow configuration of the valve element, the partial vacuum in the vial cooperates with the patient's own blood pressure to draw blood through the male connector and into the vial of the blood collection device. When the desired quantity of blood has been collected, the device may simply be disconnected from the female connector to allow the valve element to return to its distal, non-flow configuration, or closed position, thereby resealing the male connector and trapping the collected blood within the device.

It should be appreciated that in addition to the application shown in FIG. 1, the male connector 32 may be attached to other medical devices, such as a conventional female luer connector that does not have an internal valve.

It will be appreciated by those skilled in the art that the blood collection device 20 of the present invention is thus configured to allow needle free access to and collection from a patient's I.V. administration set 24 with the ease and simplicity of male-to-female luer connection and the operability of a selectively openable, pre-vacuumized collection vial achieved without the risks associated with additional vial handling and the shielded needle cannulas known and used in the art. It will be further appreciated that the device may be centrifuged as are conventional septum-covered vials and then the blood withdrawn from the collection vial the same way it was collected, through connection of the male connector with a typical female connector configured on a blood testing machine or the like. The blood may also be withdrawn by machines equipped with conventional needle cannulas by removing the male connector body member from the vial before placing the vial in the machine.

Therefore, the blood collection device of the present invention is well-suited for safe and effective blood collection from a patient's I.V. line. While a particular form of the invention has been illustrated and described, it will also be apparent to those skilled in the art that various modifications can be made without departing from the scope of the invention. For example, the circular luer opening of devices may be altered to other shapes for a customized purpose, as when specialized drugs are used. The lateral hole at the proximal end of the valve tube may have a different position or have a different number of holes. In another embodiment, there may not be a need to seal the proximal hole of the valve tube. Accordingly, it is not intended that the invention be limited except by the appended claims.

I claim:

1. A blood collection device for collecting blood from a patient through an I.V. line having a female connector, the blood collection device comprising:
   a body member having distal and proximal ends;
   a distally projecting male connector formed on the body member with an internal bore, the outer shape of the male connector configured to engage an inner shape of the female connector, the male connector having at least one lateral opening;
   a collection vial sealingly attached to the proximal end of the body member; and
   a valve element disposed within the internal bore of the male connector, the valve element having a first and a second end and including a flow passage connecting the first and second ends, the valve element also includes a flow opening disposed in the first end and the flow opening being in fluid communication with the flow passage, wherein the flow passage includes: a cross-hole formed substantially at the second end of the valve element, and an axial through-hole in fluid communication with the first end of the valve element and the cross-hole the valve element including at least one activation arm extending beyond the lateral opening of the male connector; and
   a spring device disposed at the second end of the valve element to bias the valve element toward the distal end of the male connector;
   wherein engagement of the male connector with the female connector causes the female connector to push the activation arm and the valve element toward the proximal end of the male connector thereby causing the flow opening of the valve element to open and allow fluid flow between the female connector and the collection vial, and upon disengagement of the female and male connectors, the spring device forces the valve element toward the distal end of the male connector such that the flow opening of the valve element closes when the female connector is disengaged from the male connector.

2. The blood collection device of claim 1 wherein the male connector further includes a support device disposed at its proximal end for receiving the spring device so that the spring device may bias the valve element towards the distal end of the male connector.

3. The blood collection device of claim 2 wherein:
   the spring device is configured with two spaced-apart proximally-projecting legs;
   the support device includes a spreader bar positioned between the legs; and
   the legs flexibly straddle the spreader to bias the valve element towards the distal end of the in male connector.

4. The blood collection device of claim 1 wherein the valve element includes:
   a tube having a distal end and proximal end; and
   and end cap disposed on the distal end of the tube and configured to sealingly engage the internal bore of the male connector, and the end cap having the flow opening disposed therein.

5. The blood collection device of claim 4 wherein:
   the internal bore of the valve tube includes a distal portion having a distal taper from a first inside diameter to a second inside diameter at the distal end of the body, the second inside diameter being smaller than the first inside diameter;

the end cap includes an outside diameter substantially equivalent to the first inside diameter, so that when the valve element is biased distally within the internal bore the end cap is compressed radially inward to the second inside diameter, thereby closing the flow opening.

6. The blood collection device of claim 5 wherein the flow opening is elliptical.

7. The blood collection device of claim 1 wherein:
the male connector includes two lateral openings disposed in the tubular body located opposite each other; and
the valve element includes two activation arms that extend through the respective lateral openings.

8. The blood collection device of claim 1 wherein the cross-hole is positioned in the valve element at its proximal end such that when the valve element is biased towards the distal end of the male connector, the cross-hole is sealed and when the valve element is shifted towards the proximal end of the male connector upon insertion of the male connector within the female connector, the cross-hole is exposed to allow fluid flow laterally therethrough.

9. The blood collection device of claim 1 wherein:
the male connector includes a proximally-projecting body member flange about its perimeter having an interior surface defining an inside diameter; and
the collection vial is attached to the male connector through radial engagement with the body member flange.

10. The blood collection device of claim 9 further comprising a stopper configured with a distal annular flange having an exterior surface defining an outside diameter larger than the inside diameter of the body member flange, and the stopper includes a central portion projecting proximally from the annular flange and circumferentially inset from the exterior surface of the annular flange so as to form a proximally-facing annular cavity between the central portion and the interior surface of the body member flange for sealing receipt of the collection vial, and the central portion of the stopper includes a central hole so as to be substantially aligned with the internal bore of the tubular body to allow axial movement of the valve element therethrough.

11. The blood collection device of claim 10 wherein:
the central hole of the stopper is counterbored so as to have a distal hole diameter substantially equivalent to the inside diameter of the internal bore of the tubular body and a proximal hole diameter greater than the distal hole diameter and
the cross-hole is positioned along the valve element such that when the valve element is biased towards the distal end of the male connector, the cross-hole is sealed within the distal hole of the stopper and when the valve element is shifted towards the proximal end of the male connector the cross-hole is substantially within the proximal hole diameter so as to be unsealed and allow fluid flow therethrough.

12. The blood collection device of claim 1 wherein the male connector includes a male threaded collar positioned about the tubular body for receipt of female connector.

13. A blood collection device comprising:
a male connector having proximal and distal ends, a distally projecting tubular body formed with an internal bore and at least one lateral opening, the male connector further includes a proximally-projecting support arm and a body member flange thereabout;

a stopper disposed within the body member flange so as to form a proximally-facing annular cavity between at least a portion of the stopper and the body member flange, the stopper further includes a central portion formed with a central counterbored hole so as to be substantially aligned with the internal bore of the tubular body;
a collection vial sealingly attached to the male connector through receipt in the proximally-facing annular cavity; and
a valve element installed within the internal bore of the tubular body and configured to move axially therein, the valve element including an axially extending through-hole and a proximal laterally extending cross-hole that are in fluid communication with one another, the valve element also includes at least one activation arm extending through the at least one lateral opening, and the valve element includes a proximally-projecting spring device configured to engage the support arm to bias the valve element distally within the internal bore;
wherein the proximal cross-hole is sealed by the internal bore when the valve element is biased toward the distal end of the male connector, and the proximal cross-hole is un-sealed and allows fluid to flow therethrough and into the collection vial when the valve element is moved towards the proximal end of the male connector.

14. The blood collection device of claim 13, wherein:
the spring device is configured with two adjacent proximally-projecting legs;
the support arm is positioned offset from the central axis of the body and configured with a radially-inwardly extending spreader positioned substantially adjacent the internal bore; and
the legs flexibly straddle the spreader to bias the valve element distally.

15. The blood collection device of claim 13 wherein the valve element includes:
a central post; and
a distal end cap configured to sealingly engage the internal bore and having a flow opening therein for selective fluid communication with the through-hole, the end cap being further configured such that when the valve element is biased distally within the internal bore, the end cap and internal bore cooperate to close the flow opening.

16. The blood collection device of claim 15 wherein:
the male connector includes two lateral openings; and
the valve element includes two activation arms to extend through the respective lateral openings.

17. The blood collection device of claim 15 wherein:
a distal portion of the internal bore is configured with a distal taper from a first inside diameter to a second inside diameter at the distal end of the tubular body, the second inside diameter being smaller than the first inside diameter;
the end cap is configured having an outside diameter substantially equivalent to the first inside diameter, so that when the valve element is biased distally within the internal bore the end cap is compressed radially inward to the second inside diameter, thereby closing the flow opening.

18. A method for collecting blood from a patient through an I.V. line having a female connector configured with a tubular band of a predetermined interior cross-section, including:
providing a needle free vacuumized blood collection device comprising:

a male connector having a distally-projecting tubular body including an internal bore, an exterior cross-section configured to sealingly engage the interior cross-section of the female connector and at least one lateral opening, the male connector further including a proximally-projecting support arm;

a collection vial sealingly attached to the male connector; and a valve element having a first end and a second end and a selectively sealed flow passage therethrough installed within the internal core and configured to move axially therein, the flow passage including a laterally extending cross-hole formed substantially at the second end of the valve element and an axial through-hole in fluid communication with the first end of the valve element and the cross-hole, the valve element including a flow opening at the first end in fluid communication with the flow passage and further including at least one activation arm extending through the at least one lateral opening, the valve element including a proximally-projecting spring member disposed at the second end and configured to engage the support arm to bias the valve element distally within the internal bore;

inserting the blood collection device into the female connector causing the female connector to engage the at least one activation arm and to shift the valve element proximally upon further insertion of the blood collection device, thereby opening the flow opening and exposing a portion of the flow passage to allow blood flow therethrough into the collection vial; and removing the blood collection from the female connector when the desired quantity of blood has been collected so as to disengage the activation arm and allow the spring member to shift the valve element distally, the flow opening being operative in response to the distal movement of the valve element to close, thereby preventing further flow therethrough and sealing the collected blood within the device.

19. A blood collection device for collecting blood from a patient through an I.V. line having a female connector, the blood collection device comprising:

a body member having distal and proximal ends;

a distally projecting male connector formed on the body member with an internal bore, the outer shape of the male connector configured to engage an inner shape of the female connector, the male connector having at least one lateral opening;

a collection vial sealingly attached to the proximal end of the body member; and a valve element disposed within the internal bore of the male connector, the valve element having a first and a second end and including a flow passage connecting the first and second end, the valve element also includes a flow opening disposed in the first end and the flow opening being in fluid communication with the flow passage, the valve element including at least one activation arm extending beyond the lateral opening of the male connector; and a spring device disposed at the second end of the valve element to bias the valve element toward the distal end of the male connector;

wherein engagement of the male connector with the female connector causes the female connector to push the activation arm and the valve element toward the proximal end of the male connector thereby causing the flow opening of the valve element to open and allow fluid flow between the female connector and the collection vial, and upon disengagement of the female and male connectors, the spring device forces the valve element toward the distal end of the male connector such that the flow opening of the valve element closes when the female connector is disengaged from the male connector;

wherein the male connector further includes a support device disposed at its proximal end for receiving the spring device so that the spring device may bias the valve element towards the distal end of the male connector;

wherein the spring device is configured with two spaced-apart proximally-projecting legs;

the support device includes a spreader bar positioned between the legs; and the legs flexibly straddle the spreader to bias the valve element towards the distal end of the male connector.

20. A blood collection device for collecting blood from a patient through an I.V. line having a female connector, the blood collection device comprising:

a body member having distal and proximal ends;

a distally protecting male connector formed on the body member with an internal bore, the outer shape of the male connector configured to engage an inner shape of the female connector, the male connector having at least one lateral opening;

a collection vial sealingly attached to the proximal end of the body member; and a valve element disposed within the internal bore of the male connector, the valve element having a first and a second end and including a flow passage connecting the first and second ends, the valve element also includes a flow opening disposed in the first end and the flow opening being in fluid communication with the flow passage, the valve element including at least one activation arm extending beyond the lateral opening of the male connector; and a spring device disposed at the second end of the value element to bias the valve element toward the distal end of the male connector;

wherein engagement of the male connector with the female connector causes the female connector to push the activation and the valve element toward the proximal end of the male connector thereby causing the flow opening of the valve element to open and allow fluid flow between the female connector and the collection vial, and upon disengagement of the female and male connectors, the spring device forces the valve element toward the distal end of the male connector such that the flow opening of the valve element closes when the female connector is disengaged from the male connector;

wherein the male connector includes a proximally-projecting body member flange about its perimeter having an interior surface defining an inside diameter; and the collection vial is attached to the male connector through radial engagement with the body member flange; and further comprising a stopper configured with a distal annular flange having an exterior surface defining an outside diameter larger than the inside diameter of the body member flange, and the stopper includes a central portion projecting proximally from the annular flange and circumferentially inset from the exterior surface of the annular flange so as to form a proximally-facing annular cavity between the central portion and the interior surface of the body member flange for sealing receipt of the collection vial, and the central portion of the stopper includes a central hole so as to be substantially aligned with the internal bore of the tubular body to allow axial movement of the valve element therethrough;

wherein the central hole of the stopper is counterbored so as to have a distal hole diameter substantially equivalent to the inside diameter of the internal bore of the tubular body and a proximal hole diameter greater than the distal hole diameter;

the flow passage through the valve element includes:

a cross-hole formed substantially at the second end of the valve element; and an axial through-hole in fluid communication with the first end of the valve element and the cross-hole; and the cross-hole is positioned along the valve element such that when the valve element is biased towards the distal end of the male connector, the cross-hole is sealed within the distal hole of the stopper and when the valve element is shifted towards the proximal end of the male connector the cross-hole is substantially within the proximal hole diameter so as to be unsealed and allow fluid flow therethrough.

21. A blood collection device comprising:

a male connector having proximal and distal ends, a distally projecting tubular body formed with an internal bore and at least one lateral opening, the male connector further includes a proximally-projecting support arm and a body member flange thereabout;

a stopper disposed within the body member flange so as to form a proximally-facing annular cavity between at least a portion of the stopper and the body member flange, the stopper further includes a central portion formed with a central counterbored hole so as to be substantially aligned with the internal bore of the tubular body;

a collection vial sealingly attached to the male connector through receipt in the proximally-facing annular cavity; and a valve element installed within the internal bore of the tubular body and configured to move axially therein, the valve element including an extending through-hole and a proximal cross-hole that are in fluid communication with one another, the valve element also includes at least one activation arm extending through the at least one lateral opening, and the valve element includes a proximally-projecting spring device configured to engage the support arm to bias the valve element distally within the internal bore;

wherein the proximal cross-hole is sealed by the internal bore when the valve element is biased toward the distal end of the male connector, and the proximal cross-hole is in-sealed and allows fluid to flow therethrough and into the collection vial when the valve element is moved towards the proximal end of the male connector;

wherein the spring device is configured with two adjacent proximally-projecting legs;

the support arm is positioned offset from the central axis of the body and configured with a radially-inwardly extending spreader positioned substantially adjacent the internal bore; and the legs flexibly straddle the spreader to bias the valve element distally.

* * * * *